US011854681B2

(12) United States Patent
Teucher et al.

(10) Patent No.: US 11,854,681 B2
(45) Date of Patent: Dec. 26, 2023

(54) DATA MANAGEMENT UNIT FOR SUPPORTING HEALTH CONTROL

(71) Applicant: Sanofi-Aventis Deutschland GMBH, Frankfurt am Main (DE)

(72) Inventors: Axel Teucher, Frankfurt am Main (DE); Florian Schauderna, Frankfurt am Main (DE); Jochen Sieber, Frankfurt am Main (DE); Alexandra Beer, Frankfurt am Main (DE); Frank Roethke, Frankfurt am Main (DE); Frank Flacke, Frankfurt am Main (DE); Andrew Tubb, Surrey (GB); Ashley Engelhardt, Salem, NH (US); Joseph Pomata, Salem, NH (US); Margaret Wiley, Salem, NH (US); Thora Thorgilsdottir, Salem, NH (US); Alyssa Rosenzweig, Salem, NH (US)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 11 days.

(21) Appl. No.: 16/471,936

(22) PCT Filed: Dec. 21, 2017

(86) PCT No.: PCT/EP2017/084150
§ 371 (c)(1),
(2) Date: Jun. 20, 2019

(87) PCT Pub. No.: WO2018/115316
PCT Pub. Date: Jun. 28, 2018

(65) Prior Publication Data
US 2019/0318817 A1    Oct. 17, 2019

(30) Foreign Application Priority Data
Dec. 23, 2016 (EP) .................................. 16206706

(51) Int. Cl.
*G16H 20/17* (2018.01)
*G16H 50/20* (2018.01)
*G16H 40/63* (2018.01)

(52) U.S. Cl.
CPC ............. *G16H 20/17* (2018.01); *G16H 40/63* (2018.01); *G16H 50/20* (2018.01)

(58) Field of Classification Search
CPC ........ G16H 20/17; G16H 40/63; G16H 40/67; G16H 50/20
(Continued)

(56) References Cited

U.S. PATENT DOCUMENTS 7,570,980 B2    8/2009 Ginsberg
2007/0185615 A1    8/2007 Bossi et al.
(Continued)

FOREIGN PATENT DOCUMENTS

CN    101739510    6/2010
CN    101785702    7/2010
(Continued)

OTHER PUBLICATIONS

Alsaleh, Fatemah Mohammad; Use of insulin pumps by children and young people in the management of type 1 diabetes mellitus; University of London, University College London (United Kingdom). ProQuest Dissertations Publishing, 2011. 10104885. (Year: 2011).*

(Continued)

*Primary Examiner* — Hiep V Nguyen
(74) *Attorney, Agent, or Firm* — Fish & Richardson P.C.

(57) ABSTRACT

A data management unit for supporting health control, the unit including: a processor, a data input adapted to input data and/or requests and connected to the processor, a data storage connected to the processor, wherein the processor is adapted to assign a tag referring to an event chosen from a (Continued)

group of tags comprising the fasting tag and at least one other event tag to a new data received from the data input or a measurement unit, wherein the tag is assigned either automatically by the processor and/or via the data input, wherein the fasting tag can only be assigned to the new data if a time stamp of the new data is within a predefined fasting window, wherein the predefined fasting window is stored in the data storage.

18 Claims, 6 Drawing Sheets

(58) Field of Classification Search
USPC .............................................. 705/2
See application file for complete search history.

(56) References Cited

U.S. PATENT DOCUMENTS

| | | | |
|---|---|---|---|
| 2008/0059228 | A1 | 3/2008 | Bossi et al. |
| 2010/0312580 | A1 | 12/2010 | Tarassenko et al. |
| 2011/0029324 | A1 | 2/2011 | Kondo et al. |
| 2011/0077493 | A1 | 3/2011 | Shadforth et al. |
| 2011/0152657 | A1 | 6/2011 | Bielawa et al. |
| 2012/0022353 | A1* | 1/2012 | Bashan ............ A61B 5/14532 600/365 |
| 2012/0089893 | A1* | 4/2012 | Bousamra ............ A61B 5/4839 711/E12.001 |
| 2013/0198685 | A1 | 8/2013 | Bernini et al. |
| 2014/0324800 | A1* | 10/2014 | Soni ...................... G01N 33/49 707/694 |
| 2015/0161339 | A1 | 6/2015 | Teucher et al. |
| 2015/0347707 | A1 | 12/2015 | Albisser et al. |
| 2016/0210430 | A1 | 7/2016 | Saleh et al. |
| 2020/0043586 | A1 | 2/2020 | Teucher et al. |
| 2020/0090798 | A1 | 3/2020 | Teucher et al. |

FOREIGN PATENT DOCUMENTS

| | | |
|---|---|---|
| CN | 103366323 | 10/2013 |
| CN | 104737169 | 6/2015 |
| CN | 105324079 | 2/2016 |
| CN | 105745655 | 7/2016 |
| CN | 105745656 | 7/2016 |
| CN | 105956400 | 9/2016 |
| EP | 1281351 | 3/2009 |
| EP | 2085029 | 8/2009 |
| EP | 2851821 | 3/2015 |
| EP | 2966582 | 1/2016 |
| GB | 0721117 | 12/2007 |
| JP | 2010-051720 | 3/2010 |
| JP | 2011-523478 | 8/2011 |
| JP | 2012-198860 | 10/2012 |
| JP | 2012-532316 | 12/2012 |
| JP | 2013-520279 | 6/2013 |
| JP | 2013-218699 | 10/2013 |
| JP | 2015-530896 | 10/2015 |
| JP | 2015-223497 | 12/2015 |
| JP | 2016-535606 | 11/2016 |
| JP | 2016-536680 | 11/2016 |
| JP | 2016-540229 | 12/2016 |
| JP | 2017-500963 | 1/2017 |
| KR | 20150043534 A * | 4/2015 |
| WO | WO 2008/007496 | 1/2008 |
| WO | WO 2009/053713 | 4/2009 |
| WO | WO 2009/137661 | 11/2009 |
| WO | 2010089304 | 8/2010 |
| WO | WO-2010089307 A1 * | 8/2010 ........ A61M 5/1723 |
| WO | WO 2011/002791 | 1/2011 |
| WO | WO 2011/106030 | 9/2011 |
| WO | WO 2013/154294 | 10/2013 |
| WO | WO 2014/023834 | 2/2014 |
| WO | WO 2014/174063 | 10/2014 |
| WO | WO 2015/040164 | 3/2015 |
| WO | WO 2015/040165 | 3/2015 |
| WO | WO 2015/040166 | 3/2015 |
| WO | WO 2015/055469 | 4/2015 |
| WO | WO 2016/005586 | 1/2016 |

OTHER PUBLICATIONS

PCT International Preliminary Report on Patentability in International Application No. PCT/EP2017/084108, dated Jun. 25, 2019, 11 pages.
PCT International Preliminary Report on Patentability in International Application No. PCT/EP2017/084150, dated Jun. 25, 2019, 11 pages.
PCT International Preliminary Report on Patentability in International Application No. PCT/EP2017/084152, dated Jun. 25, 2019, 12 pages.
PCT International Search Report and Written Opinion in International Application No. PCT/EP2017/084108, dated Mar. 19, 2018, 14 pages.
PCT International Search Report and Written Opinion in International Application No. PCT/EP2017/084150, dated Apr. 10, 2018, 14 pages.
PCT International Search Report and Written Opinion in International Application No. PCT/EP2017/084152, dated Apr. 10, 2018, 15 pages.
Suzuki et al., "LifeMinder : A Wearable Healthcare Management System," IEICE Technical Report, Japanese Institute of Electronics, Information and Communication Engineers, Mar. 1, 2002, 101(699): 33-38 (with English Abstract).

* cited by examiner

DATA MANAGEMENT UNIT FOR SUPPORTING HEALTH CONTROL

CROSS REFERENCE TO RELATED APPLICATIONS

The present application is the national stage entry of International Patent Application No. PCT/EP2017/084150, filed on Dec. 21, 2017, and claims priority to Application No. EP 16206706.0, filed on Dec. 23, 2016, the disclosures of which are incorporated herein by reference.

TECHNICAL FIELD

The present disclosure relates to a data management unit, a medical device, a method for operating such unit, a respective computer program and a computer program product.

BACKGROUND

Diabetes mellitus is a group of metabolic diseases in which a person has high blood sugar, either because the pancreas does not produce enough insulin, or because cells do not respond to the insulin that is produced. The treatment of diabetes concentrates on keeping blood sugar levels as close to normal ("euglycemia") as possible, without causing hypoglycemia. This can usually be accomplished with diet, exercise, and use of appropriate medications (insulin in the case of type 1 diabetes; oral medications, as well as possibly insulin, in type 2 diabetes).

Essential elements of the management of diabetes with insulin are periodic checks of the glucose concentration in the blood performed by the patients themselves, in order to obtain regular information on the progress and success of the prescribed treatment. This understanding, and patient participation is vital, since the complications of diabetes are far less common and less severe in patients who have well-managed blood sugar levels. With regard to this it has to be considered that the blood glucose level fluctuates throughout the day and is directly influenced by the amount of insulin administered, as well as lifestyle factors such as the amount and kind of food that is consumed, the exercise level and stress.

Therefore, the monitoring of the sugar level in the blood with a data management unit serves a dual purpose: on the one hand it provides the patient with information about the current status of glycemic control. On the other hand can the measured values serve as information for the patient or a healthcare professional (HCP) to determine whether an adjustment in the medication, namely the amount of insulin to be taken, is indicated.

In order to achieve these goals or to get as close as possible to the desired glycemic control, it is common practice that blood glucose measurement (BGM) values are monitored by a data management unit or a blood glucose meter comprising such data management unit once or several times during the day, following a testing regime normally prescribed by an HCP. Additionally, some data management units provide suggestions for doses of the medicament to be administered or for dose changes for example based on the present blood glucose value and ingested carbohydrates.

A special role is played by the so-called fasting blood glucose measurement value (FBG). A fasting blood glucose measurement value is derived after several hours without eating (6 to 8 hours). The fasting blood glucose measurement value is typically taken in the morning before breakfast and is the most commonly performed test among insulin treated patients as it is used to assess the quality of the titration of long-acting basal insulin or analogs such as insulin glargine.

The administered doses and/or the ingested carbohydrates may be recorded. Therefore, typically a portable monitor is used which may be able to measure the blood glucose level as well or which receives the measurement values from a blood glucose measurement device. A wireless or wired data transfer can be used to transport the results from the measurement device to the data management unit. The administered doses or other data may be provided by the user input, for example using a keyboard.

In addition to the mere monitoring of the blood glucose level diabetic individuals often have to maintain tight control over their lifestyle so that they are not adversely effected by, for example, irregular food consumption or exercise. Further the HCP needs detailed information on the lifestyle of the patient to provide effective treatment or modification of treatment for controlling the disease. In former times, one of the ways of monitoring the lifestyle of a patient with diabetes has been for the individual to keep a paper logbook of their lifestyle. Currently, a number of portable electronic devices exists that can measure glucose levels in an individual and store the levels for recalling and uploading to another computer for analysis. Further, they provide functionality for storing lifestyle data for example by using a tag or flag associated to the individual measurement value.

Document EP 2 085 029 A1 refers to a method of operating an analyte measurement device having a display, user interface, processor, memory and user interface buttons. After measuring an analyte with the analyte measurement device the measurement value is displayed and the user is prompted to select a flag to associate the flag with the value. By pressing only one of the user interface buttons once the flag with the value of the device is stored. In particular, the user is prompted whenever a measuring step indicates that an analyte value is outside a predetermined range.

Document U.S. Pat. No. 7,570,980 B2 discloses blood glucose measurement data stored in an array comprising associated time code information for each measurement and various other flags. These flags may correspond to specific time frames, date information, calibration check information etc.

From the measured and flagged values the so called effective meal average value is calculated encompassing the measurement values that occur at specific times, for example one hour before and one hour after a specified meal time.

For the insulin therapy long-acting basal insulin or insulin glargine, which are long-acting basal insulin analogues, are used. These insulin or insulin analogues are usually given once daily to help control the blood sugar level of patients with diabetes. The advantage of long-acting basal insulin or insulin glargine is that they have a duration of action of more than 24 hours or even more with a less peaked profile than NPH insulins. Thus, the profile more closely resembles the basal insulin secretion of the normal pancreatic β-cells.

Due to the almost peakless profile, basal insulin and insulin glargine can be titrated. Meanwhile, there is an array of approaches that physicians use for titration. Generally, these approaches suggest a specific dose adjustment within a specific time period until the target FBG is achieved.

Each of these algorithms comes with specific rules, e.g. that the dose should not be increased if the blood glucose value (BG value) was below 70 mg/dl (low blood sugar) in the last week.

Document EP 1 281 351 A2 describes a diabetes management system which enables glycemic control for a subject. In the document WO 2010/089304 A1 a medical device for providing information for glycemic control is described.

SUMMARY

The present disclosure mainly refers to diabetes as a health problem and the blood glucose level as the physiological parameter to be controlled in order to assess the effectiveness of the prescribed treatment. However, the disclosed embodiments may also be used with regard to other health problems and for management of other physiological parameter data like (a) blood pressure in hypertensive heart disease, (b) cholesterol or lipoprotein profile in patients with risk factors for heart disease and stroke, (c) peak flow in asthmatic patients, or (d) coagulation in patients treated for hemophilia.

Although flags or tags are nowadays widely used for data management, providing one measurement value with an associated tag or flag information is sometimes too difficult and/or time consuming for the patient. Further, it is important to make sure that the correct tag information is stored with the associated measurement value because if the information is confused the additional information which is provided with the tag to the measurement value is worthless.

For good or perfect glycemic control the dose of basal insulin or insulin glargine has to be adjusted for each individual in accordance with a blood glucose level to be achieved. Usually, the dose of insulin or insulin glargine is increased from an initial dose to a final dose over a certain time period until the specific blood glucose value, typically the fasting blood glucose (FBG) value has reached the target range. In practice, such titration can be done by the health care professionals (HCPs).

However, the patient may be empowered and trained by the HCPs to do their own titration. Such a self-titration can be supported by an intervention from a third party support or service or some intermediate combination.

In everyday use, basal insulin or insulin glargine is typically under-dosed. Thus, there remains a gap between the initial dosing and an optimal dosing for achieving perfect or almost perfect glycemic control. This has a number of negative effects which better titration could help to eliminate. For example, if patients are not titrated, their blood sugar does not come down and as a result they do not feel better in the short term. Moreover, in the long term their HbA1c remains high and their health suffers. Thus, the patients may feel that their treatment is not working, and they may lose interest in the therapy or discontinue treatment.

The present disclosure resolves the above-identified medical problems and provides a safe access to a dose helper functionality which determines and recommends an insulin dose value or a dose value of another medicament to be administered by the patient in order to reduce the probability of harm which might be caused by a wrong dose suggestion to the patient. Further, tagging of measurement values shall be made easier for the user with less probability of wrong tagging. If wrong tagging could be avoided, dose suggestion would be more precise as the assign tag of a measurement value is considered in dose calculation.

The present embodiments provide enhance precision of dose calculation and to ease tagging for the user/patient.

Some embodiments include a data management unit for supporting health control. The unit includes a processor, a data input adapted to input data and/or requests and connected to the processor, and a data storage connected to the processor. The processor is adapted to assign a tag referring to an event chosen from a group of tags comprising the fasting tag and at least one other event tag to a new data received from the data input or a measurement unit, wherein the tag is assigned either automatically by the processor and/or via the data input, wherein the fasting tag can only be assigned to the new data if a time stamp of the new data is within a predefined fasting window, wherein the predefined fasting window is stored in the data storage.

Therein, new data is for example a recent measurement value of a body parameter, e.g. a blood glucose measurement value. Tagging makes data evaluation easier and more specific.

With the tag referring to a predefined event (event tag) additional information associated with the measurement value is provided as explained above. The event tag may be provided via data input, for example manually by the user, or automatically by the processor.

Preferably, the event tag for blood glucose measurement values comprises the fasting tag and at least one other tag referring to one of the following events: the event nil (no-tag), pre-meal, post-meal, pre-meal breakfast, post-meal breakfast, pre-meal lunch, post-meal lunch, pre-meal supper, post-meal supper, night time and exercise.

The time stamp associated to each new data value, preferably by a clock unit connected to the processor, comprises date and time information of a certain time point during the measurement process resulting in the respective measurement value, for example the completion of the measurement process or receipt of the new measurement value by the data management unit.

Usually the time stamp is associated by the measurement unit and is transferred to the processor with the respective measurement value. In case the new measurement value is not associated with a respective time stamp by the measurement unit the time stamp is assigned by the processor after receipt of the measurement value.

For example the following time ranges for tagging preselection may be defined:
  pre-meal breakfast: 5:00 a.m. to 8:59 a.m.
  fasting: 4:00 a.m. to 9:59 a.m.
  post-meal breakfast: 9:00 a.m. to 10:59 a.m.
  pre-meal lunch: 11:00 a.m. to 11:59 a.m.
  post-meal lunch: 12:00 p.m. to 3:59 p.m.
  pre-meal supper 4:00 p.m. to 6:59 p.m.
  post-meal supper: 7:00 p.m. to 8:59 p.m.
  night time or bedtime: 9:00 p.m. to 11:59 p.m.
  exercise: 3:00 p.m. to 8:00 p.m.

At least part of the time ranges for tagging preselection may be set and changed by the user and/or HCP using for example the settings menu of the data management unit.

The time range for tagging preselection for the at least one predefined event refers to a time range which is used to support the user during tagging as follows. After receipt of a new measurement value of the physiological parameter and assignment of an associated time stamp, if necessary, the processor compares the time information of the associated time stamp with the time range for tagging preselection. If the time information lies within the time range, the corresponding tag of the predefined event is automatically selected and provided at the display for user confirmation. For example, if the current time range for the fasting blood glucose tag comprises the range between 4:00 a.m. and 9:59 a.m. as indicated above, than for each measurement value measured within this time range the fasting tag is automatically selected (preferably if no other measurement value of that day comprises the fasting tag) and may be confirmed by the user afterwards as described below in detail. It is further possible for the user to change the automatically selected tag or to select the no-tag.

Hence, as a tag is automatically selected and only needs to be confirmed by the user the inventive data management unit reduces the number of steps for tag selection. Accordingly, it is easier for the user to assign a tag with the measurement value. Further, as the most probable tag according to the time stamp of the measurement value is automatically selected the inventive data management unit reduces the possibility for incorrect tagging.

In an alternative embodiment the processor is adapted to automatically select the tag of one of the at least one meal event or the fasting tag after one of the tags "before meal" or "after meal" was selected by the user. In this embodiment the data storage comprises the time ranges for tagging preselection of the meals, only, for example "breakfast", "lunch" and "dinner". Preferably, the "fasting" time range for tagging preselection is also provided. This embodiment also supports the user during tagging and reduces the risk of erroneous tagging as well. Additionally, the number of time ranges for tagging preselection is reduced so that it is less time consuming to pre-set these time ranges and to choose the correct tag. In this case the tag is a composite tag with a first component "before meal" or "after meal" and a second component referring to the particular meal. In a further embodiment the confirmation of the second component referring to the particular meal may not be requested by the user. The processor selects the meal component of the tag without user confirmation. In this case only a query for user input of the corresponding selection (i.e. a user confirmation) of the first tag component "before meal" or "after meal" is provided.

In an embodiment the time range for tagging preselection of a certain event may be different for working days and non-working days. In this case the determination whether the associated time stamp of the new measurement value is within the time range for tagging preselection is based not only on the time information of the time stamp but also on the date information.

According to the invention, the fasting tag can only be assigned (automatically) to the new data if the time stamp of the new data is within a predefined fasting window (preferably at a predefined time range around a predefined usual fasting time), wherein the predefined fasting window (and if applicable also the predefined usual fasting time) is stored in the data storage. This means that it is not allowed to assign the fasting tag for a new data value with a time stamp outside the fasting window. In this case, for example, the fasting tag is not shown in the menu at the display where the user can choose the suitable tag. Thereby the risk for wrong dose helper guidance is reduced as the dose helper is based on fasting measurements (mainly or only). The risk mitigation measure aims at reducing the possibility for incorrect use of the fasting tag and reducing the number of user steps so that the usability of the device is enhanced.

For example, the fasting window may be + and −3 hours around the usual predefined fasting time (e.g. 7 a.m.), wherein the predefined fasting time and predefined fasting window are preferably stored in the data storage. The advantage of this embodiment is that the number of steps and/or button presses for tagging is reduced as in the time range outside the fasting window the fasting tag is not an option. In another example, the fasting tag is assigned via data input, only. Preferably, the predefined usual fasting time can be adjusted by the user at any time. Additionally, in one embodiment the meal time ranges for tagging preselection have to be confirmed by the user when the predefined usual fasting time is changed as it is expected that with a change in fasting time also the meal times may change according to a change in user's habits.

In another embodiment the display displays a predefined definition screen when at the first time the fasting tag is to be assigned to a new data via the data input, wherein the user has to confirm the definition screen before the assignment of the fasting tag to the new data is completed. This makes the user understand what to tag a reading as "fasting", thereby avoids incorrectly tagged fasting readings and leads to further risk mitigation. Therein the screen may be shown if the reading is tagged at a minimum of a predefined time range from the usual fasting time (e.g. 4 hours from the usual fasting time) or outside the predefined fasting window (e.g. minimum of 1 hour outside the fasting window). Additionally or alternatively, the screen is shown if "fasting reading shortly after an after-meal reading". In this case, for example, if at the same day a measurement value was already marked as e.g. "after breakfast" two hours ago and the user attempts to mark the new data value now as "fasting" this is unlikely. Since fasting should be no glucose for at least last 8 hours, the after-meal tag suggests that the last meal was approximately 4 hours ago.

In another embodiment, the processor further comprises a dose helper adapted to provide a dose helper functionality with regard to a predefined medicament, wherein the data storage adapted to store a usual dose time and/or a dose time window, a predefined recommendation message, a time of a dose helper request, a predefined criterion, wherein the clock unit is adapted to determine the absolute time of a dose helper request received by the data input, wherein the processor is adapted to initiate storing at least the time of a dose helper request that is outside the time range around the usual dose time in the data storage, wherein the processor is further adapted to execute the dose helper functionality only if the time of the most recent dose helper request is within the dose time window around the usual dose time, wherein the processor is further adapted to initiate sending a recommendation message for change of usual dose time and/or dose time window to the display if the time distribution of most recent dose helper requests within a predefined time period corresponds to the predefined criterion.

The advantage of this embodiment of a data management unit consists therein that the use of dose helper restricted to a period around 'usual dose time' when it is safe and in compliance with the therapy. Hence, the risk of inappropriate use of the dose helper is reduced. The absolute time is the local time at the current location of the user/patient who is going to execute the dose helper by inputting the dose helper request. Preferably, the predefined time period and the data regarding the criterion are stored in the data storage.

The dose helper functionality according to the present invention refers to a titration method which determines and/or recommends a medicament dose value or its corrective amount, preferably a basal long-acting insulin dose value, to be administered by the patient, based on a measured physiological parameter, preferably based on measured blood glucose values, more preferably based on measured FBG values, and/or information about hypoglycemic and/or hyperglycemic events and/or other data which starts at a starting dose and guides the patient step by step to a final dose of basal long-acting insulin that keeps the patient in a predefined target glucose level. Preferably, the dose helper functionality is realized as a computer program unit fully separate, for example, from a unit that determines a blood glucose value. The dose helper functionality may be terminated by the user and/or the HCP and/or the program itself, for example if the program detects missing compliance of the patient. After termination the dose helper functionality may be reinitialized and reactivated again by an initialization and activation procedure.

The term "medicament", as used herein, means a pharmaceutical formulation containing at least one pharmaceutically active compound.

In one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, In a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis.

In a further embodiment the pharmaceutically active compound comprises at least one peptide for the treatment and/or prophylaxis of diabetes mellitus or complications associated with diabetes mellitus such as diabetic retinopathy.

In a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gn-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-N H2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(02)25, Asp28] Exendin-4(1-39),
des Pro36 [Trp(02)25, IsoAsp28] Exendin-4(1-39),
des Pro36 [Met(O)14 Trp(02)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(02)25] Exendin-4(1-39)-NH2,
H-(Lys)6-des Pro36, Pro37, Pro38 [Trp(02)25, Asp28] Exendin-4(1-39)-NH2,
H-Asn-(Glu)5-des Pro36, Pro37, Pro38 [Trp(02)25, Asp28] Exendin-4(1-39)-NH2,
des Pro36, Pro37, Pro38 [Trp(02)25, Asp28] Exendin-4 (1-39)-(Lys)6-NH2,
H-(Lys)6-des Pro36, Pro37, Pro38 [Trp(02)25, Asp28] Exendin-4(1-39)-(Lys)6-NH2,
H-Asn-(Glu)5-des Pro36, Pro37, Pro38 [Trp(02)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(02)25, Asp28] Exendin-4(1-39)-Lys6-NH2,
H-des Asp28 Pro36, Pro37, Pro38 [Met(O)14, Trp(02)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (02)25, Asp28] Exendin-4(1-39)-NH2, des Pro36, Pro37, Pro38 [Met(O)14, Trp(02)25, Asp28] Exendin-4(1-39)-(Lys)6-NH2, H-(Lys)6-des Pro36, Pro37, Pro38 [Met(O)14, Trp(02)25, Asp28] Exendin-4(S1-39)-(Lys)6-NH2, H-Asn-(Glu)5-des Pro36, Pro37, Pro38 [Met(O)14, Trp (02)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

In an embodiment of the present disclosure, the processor is further adapted to check as the above mentioned criterion whether the number of most recent dose helper requests outside the dose time window is higher than the predefined maximum number during the predefined time period, wherein the predefined number is stored in the data storage. Therein, a predefined number is for example 3, 5, or 7, a predefined time period is for example 1 month. If the number of most recent dose helper requests outside the dose time window is higher than the predefined maximum number, a respective warning information (see below) is generated by the display and/or its sound generator and/or its vibration generator and provided to the user.

In another embodiment of the present disclosure, the processor is further adapted to generate and send a predefined warning information for further risk mitigation, preferably to the display, if it receives a dose helper request from the data input that is outside the dose time window, wherein the predefined warning information is stored in the data storage. Therein, the warning information may be a message and/or a sound and/or a tactile signal.

In another embodiment the processor is further adapted to automatically calculate a modified value of a usual dose time and/or dose time window based on the time of at least a part of the most recent dose helper requests, preferably within the predefined time period, wherein the recommendation message recommends to change the usual dose time and/or the dose time window according to the respective calculated modified value. This allows easier handling and saver change of the usual dose time and/or dose time window.

In a further embodiment the processor is further adapted to send a predefined reminder message to the display if a predefined part of the dose time window is passed at the current day without input of a dose helper request or finishing the requested dose helper functionality, wherein the received reminder message is displayed at the display. The reminder message may be an audible signal and/or a visual signal and/or a tactile signal (vibration). Further, the predefined part of the dose time window may be for example 50%, 70% or 90% of the dose time window. Additionally, if the dose helper was run already on the same day no reminder message is sent to the display. The advantage of this embodiment consists therein, that the user is further supported in using the dose helper.

In a further embodiment the processor is further adapted to receive a data input from the user related to the physiological parameter, wherein the data input comprises at least one of the following parameters:
  occurrence or number of hypoglycemic events after a predetermined point in time, e.g. a last use of the medical device or the time stamp of the last (previous) measurement value,
  occurrence or number of hyperglycemic events after a predetermined point in time, e.g. the last use of the medical device or the time stamp of the last (previous) measurement value,
  size of the injected medicament dose after a predetermined point in time, e.g. the last use of the medical device or the time stamp of the last (previous) measurement value, wherein preferably the injected medicament dose is automatically selected as the dose of the last (previous) suggested dose.

The above mentioned data input may be facilitated after tagging or during titration.

These additional parameters may be used for further calculations, data display, for the assessment of the disease or for the titration algorithm. Additionally, the preselection of the dose as the last suggested dose reduces the risk for erroneous dose data.

In another embodiment, in particular in the case in which the dose helper functionality (titration method) is realized as an app within a smartphone, an internet connection, a GSM connection, a GPS receiver or other means for determining the actual location and/or the time-zone of the device may be provided. Hence, the device comprises for example a GSM receiver, a GPS receiver or module, a radio broadcast receiver capable of interpreting an RDS signal and/or a radio clock receiver like DCF 77 in order to determine the local time. Further, in case that the method is realized as an app within a smartphone a built-in GPS module may determine its location using public hotspots. The dose helper functionality of the device may provide a warning display and/or may not calculate a dose suggestion or dose increase in case that these means for determining the location of the device assess that the location of the device has changed to a time zone, where the time change is more than a predefined maximum time change value, for example more than three hours. A patient facing a time change larger than the predefined maximum time change is assumed to have difficulties meeting the requirements of dose administration intervals for long-acting insulin and fasting time for determining correct FBG values and the patient may be locked out from the dose helper functionality.

The data management unit may therefore keep track of the time, e.g. by implementing an electronic timer, or a first clock and calendar function. To enable tagging of a glucose measurement as a fasting glucose measurement, the device may have to determine, whether the last blood glucose measurement that was related to a meal, such as the "after dinner" glucose measurement, dates back at least, for example, eight hours. In order to determine this time difference correctly without influence of time change because of travelling, the device may have to account for time shifts that may occur for example when travelling to a different time zone. For this purpose, the device may comprise a separate second clock which is separate from the clock showing the actual time to the user. In order to determine a time difference reliably, the second clock may not be adjustable by the user. The second clock may derive its energy from a separate battery (for example a coin cell) which is separate from the battery or other energy source of the device and in particular separate from the energy source of the first clock.

In another embodiment, the data storage stores at least one predefined primary information and at least one predefined secondary information assigned to the at least one predefined primary information, wherein the processor is further adapted to send the one of the at least one predefined primary information and additionally the at least one predefined secondary information to the display, wherein the at least one predefined primary information and the at least one predefined secondary information are displayed on one screen of the display. The advantage of this embodiment consists therein that it is avoided to confuse the user and to save time for the user in reading information (error) messages, in particular if several conditions for information messages apply, the user is provided with a single message giving one instruction and all reasons for this instruction.

The primary information and the secondary information belong to each other in the way that the secondary information depends on the primary information. For example, the primary information contains an instruction to the patient, whereas the secondary information contains a reason or cause for this instruction. The secondary information is not displayed if the primary information is not displayed. Preferably, there is more than one secondary information belonging to one specific primary information. All predefined primary and secondary information is stored in the data storage.

In a further embodiment of the above, if more than one predefined secondary information is assigned to the primary information, each secondary information applicable is displayed with the predefined primary information displayed only once. The information could be an instruction to the user, a suggestion to the user or a description of a cause for a distinctive behavior of the unit. Further, the user may be asked for confirmation of the primary and secondary information.

In another embodiment, if two or more secondary information is displayed on the one screen of the display the secondary information is displayed according to its priority with regard to importance for the respective user or the user type. Therein, a user type could be e.g. patient or HCP. Further, an importance level is predefined and stored in connection with each secondary information, in a preferred embodiment the importance level is defined and stored for each user type.

Analogously, the above problem is also solved by a medical device comprising the above explained data management unit with the same advantages.

The present disclosure provides a method for operating a data management unit for supporting health control, the unit comprising: a data input adapted to input data and/or requests and connected to the processor, a data storage connected to the processor, wherein the processor assigns a tag referring to an event chosen from a group of tags comprising the fasting tag and at least one other tag to a new data received from the data input or a measurement unit, wherein the tag is assigned either automatically by the processor and/or via the data input, wherein the fasting tag can only be assigned to the new data if a time stamp of the new data is within a predefined fasting window, wherein the predefined fasting window is stored in the data storage.

The present disclosure provides a computer program for operating a data management unit, the unit comprising: a data input adapted to input data and/or requests and connected to the processor, a data storage connected to the processor, wherein the program is adapted to execute the step that a tag referring to an event chosen from a group of tags comprising the fasting tag and at least one other tag is assigned to a new data received from the data input or a measurement unit by the processor, wherein the tag is assigned either automatically by the processor and/or via the data input, wherein the fasting tag can only be assigned to the new data if a time stamp of the new data is within a predefined fasting window around a predefined usual fasting time, wherein the predefined fasting window and the predefined usual fasting time is stored in the data storage.

The above method and computer program may be realized with the embodiments as mentioned above with regard to the above inventive data management unit.

The above problem is further solved by computer program product comprising a computer-readable medium bearing computer program code embodied therein for use with a computer, wherein the computer program code comprises the above mentioned computer program.

The above-mentioned advantages as well as other advantages of various aspects of the present invention will become apparent to those of ordinary skill in the art by reading the following detailed description with the explanation of the accompanying drawings. All features described above and below and/or illustrated per se or in any combination form the subject-matter of the invention, independent of their inclusion in the claims or their back-reference.

BRIEF DESCRIPTION OF DRAWINGS

Exemplary embodiments of the present invention are described herein with reference to schematic drawings, in which.

DETAILED DESCRIPTION

The following paragraphs will describe various embodiments of the present disclosure. For exemplary purpose only, the embodiments are outlined in relation to a medical device with regard to blood glucose level measurement. However, the used terminology and the description of the embodiments with respect to the medical device or the method are not intended to limit the principles and ideas of the invention to such a single device or method and may be adapted to other physiological values accordingly.

Figure 1:
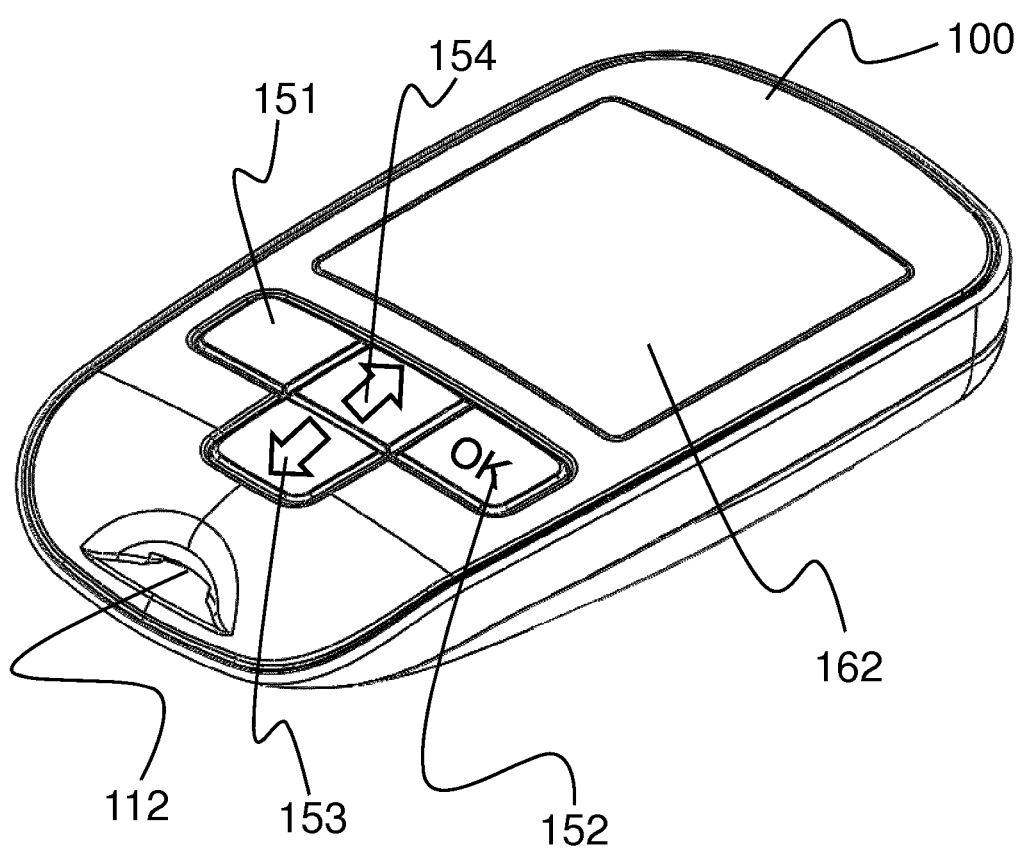
FIG. 1 shows a medical device according to an embodiment of the present disclosure in a perspective view.
Figure 2:
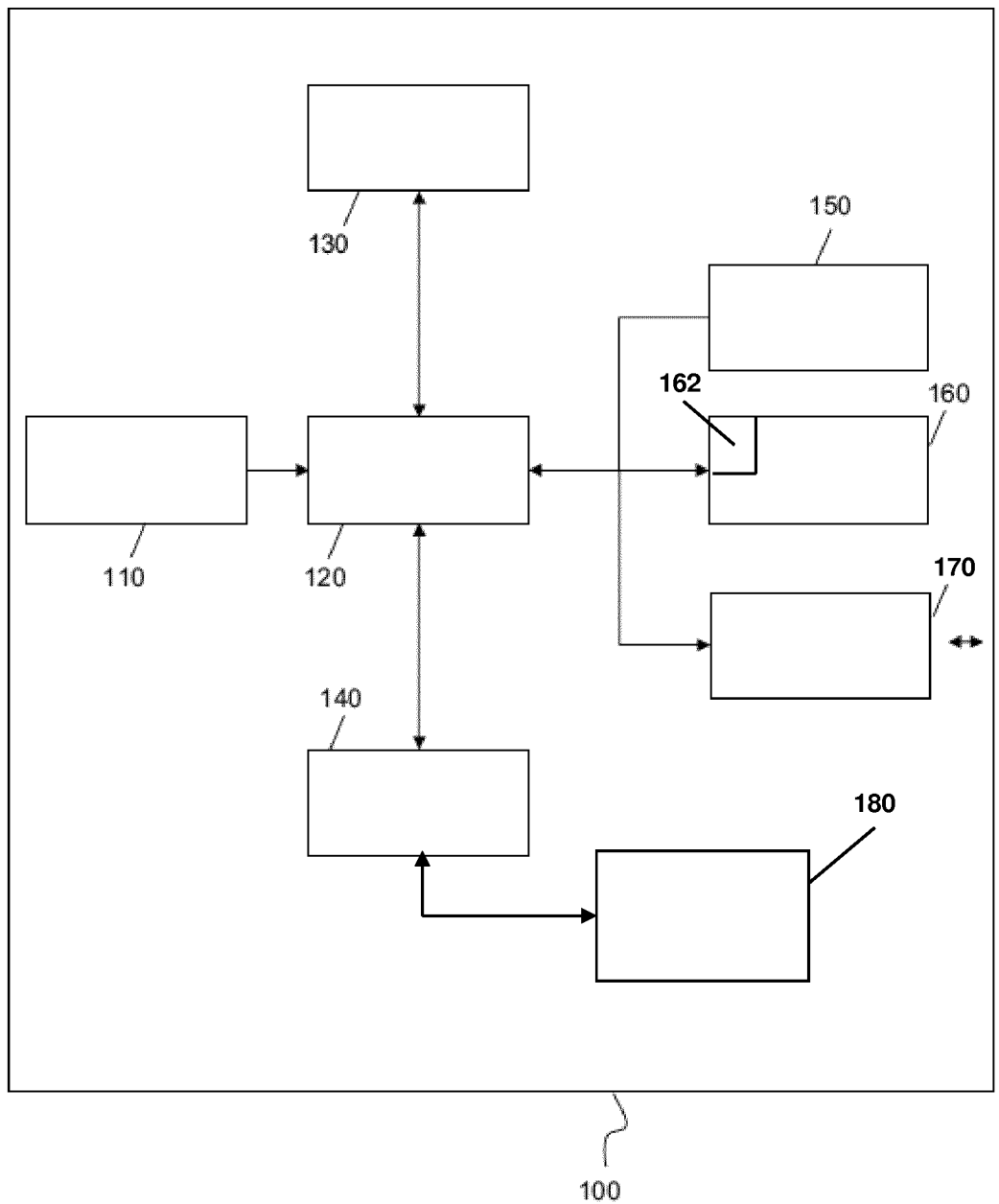
FIG. 2 shows a diagram of the medical device as shown in FIG. 1.

FIG. 1 is a schematic drawing and FIG. 2 is a schematic diagram of the medical device 100 according to an embodiment of the present disclosure. Preferably, the medical device 100 comprises a blood glucose measurement unit 110, which is arranged to measure the blood glucose level. Further, the measurement unit 110 comprises an interface and a slot 112 for inserting a test strip.

The blood glucose measurement unit 110 is connected to a receiving unit 120, which is arranged to forward e.g. blood glucose measurement data received from blood glucose measurement unit 110 to a data storage 130 (storage unit or means) or memory, such as a Flash memory. Alternatively, the receiving unit 120 may retrieve stored data such as e.g. blood glucose value data from the data storage 130 and forward it to a processor 140 (processing unit or means), such as a microcontroller or microprocessor or any other functional unit capable of processing data, a digital signal processor, and/or the like. Alternatively, the receiving unit 120 directly forwards the blood glucose value data received from the blood glucose measurement unit 110 to the processor 140.

Receiving unit 120 is further connected to a user input unit 150 of a user interface. The user input unit 150 is arranged to receive input from the user of the medical device 100 for example by key 151, confirmation key (OK button) 152, key 153 for scrolling down (downward button) and key 154 for scrolling up (upward button). The user input data are forwarded from the user input unit 150 to the receiving unit 120, which either forwards it to the processor 140 or to the data storage 130.

Furthermore, the user interface of medical device 100 comprises a display unit 160 with a display 162, which is connected to the receiving unit 120 as well. Preferably, the display unit 160 receives data to be displayed by the display 162 from the receiving unit 120 or the processor 140.

Preferably, the medical device 100 additionally comprises a further interface 170, for example a wired interface such as a serial port, a Universal Serial Bus (USB) interface, a mini-USB interface, or a wireless interface such as an infrared (e.g. an IRDA) interface, a Bluetooth™ interface, and/or the like, in order to receive data and/or to transmit data. The interface 170 is preferably connected to the receiving unit 120 in order to receive data from the receiving unit 120 and/or to forward data to the receiving unit 120.

Additionally, the medical device 100 comprises a clock unit 180 which provides a date and time information, preferably based on a clock generator, which may be displayed at the display 162. Further, the clock unit 180 provides date and time information in particular for generating a time stamp for an associated blood glucose measurement.

The receiving unit 120, the data storage 130, the processor 140, the input unit 150, the display unit 160, the clock unit 180, and optionally the interface 170 form the data management unit according to the present disclosure.

As outlined above, the medical device 100 preferably comprises the blood glucose measurement unit 110. Preferably, the blood glucose measurement unit 110 is arranged to measure the blood glucose level in the blood of e.g. the user by testing a drop of blood on a test strip that is inserted into the slot 112. The measurement may be conducted using e.g. a well-known electrochemical method. Full insertion of the test strip in the slot 112 may be detected by a respective sensor. The measured blood glucose value is transformed to blood glucose value data and forwarded preferably immediately or on demand to the receiving unit 120. Alternatively, the blood glucose measurement unit 110 is arranged to measure the blood glucose level of the user via infrared diagnosis or an alternative contactless measurement method.

According to a further alternative (not depicted in FIG. 1) the blood glucose measurement unit 110 is implanted in the body of the user of the medical device and forwards the data to the receiving unit 120 either via a wired connection or via a wireless connection. In an embodiment, such an implanted blood glucose measurement unit 110 is a continuous measurement sensor e.g. based on a chip which may allow a continuous closed loop control. In the latter case the medical device comprises two parts, one part contains the measurement unit 110 and the other part the remaining units of the medical device, i.e. the data management unit. The blood glucose measurement unit 110 preferably forwards the blood glucose measurement value data to the receiving unit 120 via interface 170. According to a further alternative the medical device does not comprise a blood glucose measurement unit which measures the blood glucose values but only the data management unit, and receives blood glucose value data from an external unit.

The measurement of the blood glucose measurement is preferably triggered by the receiving unit 120 which sends a respective signal to the blood glucose measurement unit 110. According to one preferred alternative the receiving unit 120 receives a trigger signal generated by user input which is received via user input unit 150 or based on a signal from the slot 112 detecting a test strip. Alternatively, the trigger signal is generated automatically by the clock unit 180 or by the processor 140. Further alternatively, only the transmission of measurement values is triggered by the user input or the processor 140 via the user input 150.

Preferably, the receiving unit 120 is represented e.g. by the input ports and output ports of a microprocessor or a bus system managing the data handling between several functional units. This includes bus systems, such as e.g. Advanced Microprocessor Bus Architecture bus systems implemented in a microprocessor or external bus systems connected to a microprocessor. Via the receiving unit 120, data are retrieved from the data storage 130 on demand and forwarded to the processor 140, to the display unit 160 or to the interface 170. Moreover, the receiving unit 120 forwards control signals, such as trigger signals or control signals e.g. to the blood glucose measurement unit 110, the display unit 160 or the interface 170.

The data storage 130 is arranged to store data entered via the user input unit 150, a plurality of blood glucose measurement data received from the blood glucose measurement unit 110 together with the time stamp and/or at least one event tag associated to each measurement data, data calculated from the plurality of blood glucose measurement values processed by the processor 140 and/or data received via interface 170.

Further the data storage 130 stores parameter data like an associated time range for tagging preselection regarding for example a fasting tag. Preferably such a time range is defined using a center time and a duration, wherein the time range comprises the time around the center time with the size of the duration in both directions. For example, the predefined fasting window for assigning the fasting tag is defined with a duration of 3 hours and a predefined usual fasting time at 7 a.m., so that the time range for fasting tagging preselection encompasses the time between 4:00 a.m. and 9:59 a.m.

Additionally, for example the data storage 130 stores the following preset time ranges for pre- and post-meal times for tagging preselection:
pre-meal breakfast: 5:00 a.m. to 8:59 a.m.
post-meal breakfast: 9:00 a.m. to 10:59 a.m.
pre-meal lunch: 11:00 a.m. to 11:59 a.m.
post-meal lunch: 12:00 p.m. to 3:59 p.m.
pre-meal supper. 4:00 p.m. to 6:59 p.m.
post-meal supper: 7:00 p.m. to 8:59 p.m.
night time or bedtime: 9:00 p.m. to 11:59 p.m.

Predefined mealtime time ranges, the usual fasting time and the fasting window may be set by the user "Settings" mode of the medical device 100 at any time.

Alternatively, the data storage 130 stores the following user-settable time ranges for tagging preselection with regard to meal times:
breakfast: 5:00 a.m. to 10:59 a.m.
lunch: 11:00 a.m. to 3:59 p.m.
supper: 4:00 p.m. to 8:59 p.m.

Furthermore, data storage 130 is arranged to provide the stored data to the processor 140, to the display unit 160 and/or to the interface 170. The data storage 130 is preferably implemented as a semiconductor memory such as a Flash memory. Alternatively, it is implemented as a hard disk memory or an on-chip memory of the processor 140.

The data storage 130 also stores predefined data, which at least partly may be changed by the user, such as above mentioned time ranges for tagging preselection for a number of pre-set events, a usual dose time, a dose time window, a maximum number of dose helper requests outside the dose time window, a time period for dose helper request check, warning messages for the user, e.g. a warning message if the dose helper request is received outside the dose time window, a dose helper reminder message, a value determining the part of the dose time window after its passing the dose helper reminder message is displayed, data for a definition screen for the fasting tag, at least one primary information such as an instruction to the user, a suggestion to the user, a description of a cause for a distinctive behavior of the device, and secondary information associated with at least one primary information.

The user input unit 150 is preferably implemented as a keyboard comprising one or more push buttons 151, 152, 153, 154. The keyboard may comprise one or more soft keys, wherein the function of the soft keys may be displayed on the display 162. Alternatively, the user input unit 150 is a key board or a touch screen. Alternatively, the user input unit 150 comprises a microphone for receiving speech input so that data can be entered via speech input.

After facilitating a blood glucose measurement a tag may be automatically associated to the measurement value referring to lifestyle data as explained below in detail. The automatically selected tag may be changed by pressing the up or down keys 153, 154 scrolling upwards or downwards through the different tags which are for example the fasting tag, pre-meal tag, post-meal tag and no-tag, respectively, referring to a measurement value which is a fasting blood glucose value, a pre-meal blood glucose value, a post-meal blood glucose value and a blood glucose value that cannot be associated to one of the previous lifestyle parameter.

The display unit 160 preferably comprises an LCD or LED display 162. Preferably, the display displays a number of alphanumerical characters so that e.g. the presently measured blood glucose value can be displayed together with additional instructions for the user. Alternatively or additionally, the display unit 160 comprises a graphic display in order to display graphs or graphics such as icons. Further the display of the display unit 160 may comprise a touchscreen.

The interface 170 is preferably a wireless interface, such as IRDA, Bluetooth™, GSM, UMTS, ZigBee, or WI-FI, etc. Alternatively, the interface is a wired interface, such as a USB port, mini-USB port, serial data port, parallel data port, etc., for receiving and transmitting data. In a further alternative embodiment the medical device 100 does not comprise an interface 170.

According to another alternative embodiment, medical device 100 comprises a memory card reader or a memory card reader interface. The memory card reader is preferably adapted to read information from a memory card, such as a Flash memory card, or any type of SIM card. For this purpose, the memory card comprises a memory, wherein at least one of a selected algorithms together with corresponding parameters, a history of the blood glucose values and/or insulin doses administered, etc. is stored. Thus, in the case that the medical device 100 has a defect, the relevant data may still be stored on the memory card which can be easily removed from the memory card reader of the medical device 100 and transferred to a new medical device 100. Moreover, the memory card 100 may be used in order to provide information on the history of the treatment to e.g. an HCP.

In the case that the memory card is a SIM card providing subscriber identification for a mobile communication network and the interface unit 170 is additionally a mobile communication interface, additional functions of the medical device 100 can be unlocked by the provider of the SIM card via a telecommunication channel. This offers the possibility that the medical device 100 can communicate with other telecommunication devices via predefined channels, such as UMTS or GSM. Via the international mobile subscriber identity, also called IMSI, stored in the SIM card, the medical device 100 identifies itself within the network and, thus, can be addressed via the network. In such a case the medical device 100 can be easily checked, remote controlled, updated, monitored, etc., via interface unit 170, e.g. by addressing the mobile communication unit with a phone number.

Furthermore, the medical device 100 is able to transmit data via SMS, e-mail or via mobile internet connection. Moreover, this offers the possibility to locate the medical device 100 in an emergency case.

In the case that the blood glucose measurement unit 110 is a sensor which is e.g. implanted a dose delivery unit with an insulin pump forming an automatic delivery system may be additionally provided.

Figure 5:
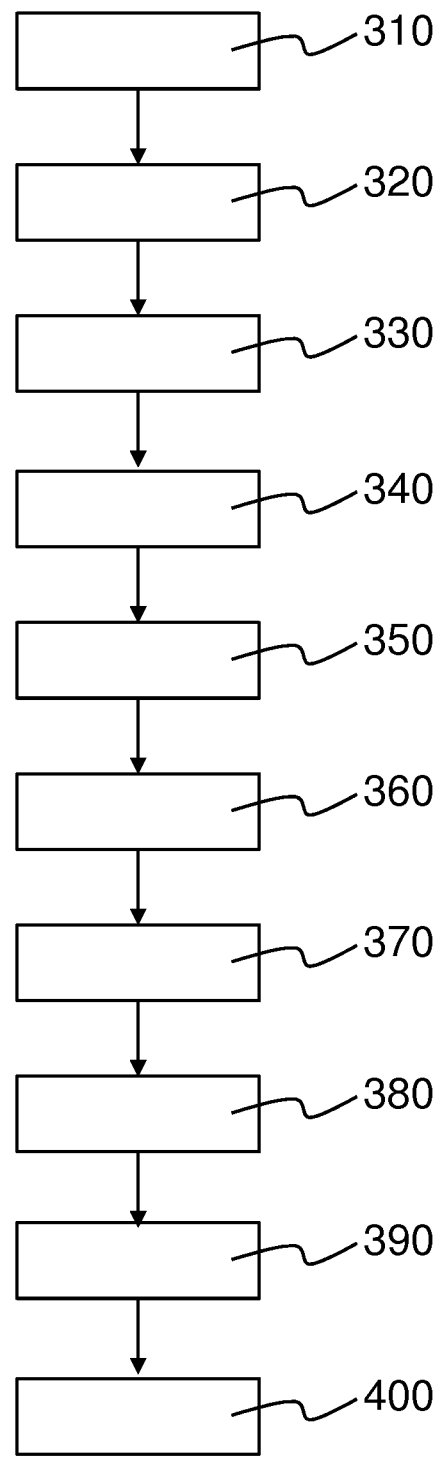
FIG. 5 depicts a flow diagram of a method realized by the inventive medical device in the "Measure BG" mode.

As shown in FIG. 5, the medical device 100 or the data management unit is capable to perform a number of process steps. According to one embodiment after switching on, e.g. by pressing a key 151, 152, 153 or 154, preferably the confirmation key 152 for a predetermined time, or detection of a test strip within the slot 112, the medical device 100 performs initialization step 310 for initializing the functional components of the medical device 100. After this, the different operation modes which are implemented in the medical device 100, are displayed in the display step 320, preferably operation modes such as "Measure BG", "Logbook", "Settings" and/or "Titration".

In step 330 the user selects one of the displayed operation modes via the user input unit 150, for example by means of the keys 153, 154 for scrolling down or up, and confirms the selection using the confirmation key 152.

In step 340 the selected operation mode is executed. As an example the mode "Measure BG" is selected for executing a blood glucose measurement. Upon execution of this mode the user/patient is requested to provide a test strip with a blood sample.

In the "Logbook" mode the history of previous measurements and statistical results may be calculated and displayed.

The "Settings" mode allows the user to define and change some parameters of the medical device 100 stored in the data storage 130, e.g. time ranges for tagging preselection for a number of pre-set events, the usual dose time, the dose time window, the maximum number of dose helper requests outside the dose time window, the time period for dose helper request check, the value determining the part of the dose time window after its passing the dose helper reminder message is displayed, the usual fasting time, and/or the fasting window.

In the "Titration" mode a dose suggestion may be provided by the medical device 10 for basal insulin or analogue by using the dose helper functionality.

After selecting the mode "Measure BG", in step 350 a drop of blood is applied to the test portion of the test strip which is inserted in slot 112 of the medical device 100.

According to an alternative version of the operation process steps 310 to 340 may be skipped in the case that a specific operation mode is preselected. In this case, after initialization, the preselected operation mode, which is either preselected by the user or automatically selected in accordance with a specific event, for example the detection of a fully inserted test strip in slot 112, the operating process proceeds with the following step 350 and asks the user to apply a drop of blood. In step 360 it executes the preselected one or more operation modes, for example the mode "Measure BG".

Now in step 360 the measurement unit 110 determines e.g. by a known electrochemical or an optical method the blood glucose level and displays the respective new measurement value at the display 162.

In the next step 370 the clock unit 180 generates a time stamp of the present measurement comprising a date and time information of the absolute time of the measurement (e.g. its finishing) determined by the clock unit 180. The time stamp is also displayed in display 162 and both, the present blood glucose measurement value and the associated time stamp is transferred by receiving unit 120 to the data storage 130.

In the next step 380 the processor 140 compares the absolute time of the time stamp of the present blood glucose measurement value with the time ranges for tagging preselection of the events stored in the data storage 130. If the time stamp of the present measurement value (new measurement value), in particular the time information of the time stamp, lies within the current time range of e.g. the fasting window around the usual fasting time or the post-meal lunch event automatically the fasting tag or the post-meal lunch tag, respectively, is provided for confirmation by the user and displayed with a respective sign 168, for example a struck out, empty apple or a bitten apple, respectively, at display 162 (see FIG. 3).

Figure 4:
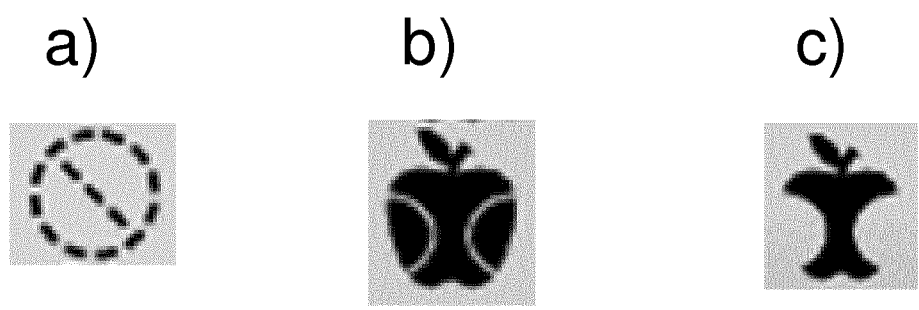
FIG. 4 shows further examples of tag signs as they are displayed on a display of the medical device as shown in FIG. 1.

Alternatively in step 380, the user selects one of the event tags "pre-meal" and "post-meal" represented by a full apple as shown in FIG. 4b) in case of the pre-meal tag and represented by a bitten apple as shown in FIG. 4c) in case of the post-meal tag and confirms the tag. Then, the processor 140 automatically selects the associated meal according to the above time range for meal times according to the time information of the time stamp, preferably without further user confirmation. For example, the processor selects "supper" if the time information of the present time stamp is 7:35 p.m. Accordingly the tag comprises the information "pre-meal" or "post-meal" and "supper" and forms a composite tag which is then stored in the data storage 130 initiated by the processor 140.

In order to show that a confirmation is necessary the tag sign 168 displayed on display 162 is blinking/flashing. Now, the user may confirm the fasting tag for example by pressing the confirmation key 152. Alternatively, the user may change the tag using the up and down keys 153, 154 into the pre-meal tag, the post-meal tag or the no-tag (nil). If the correct tag is chosen the user confirms the tag by pressing the confirmation key 152. By confirmation of the tag with the confirmation key 152 the flashing of the displayed tag sign is stopped and the tag sign is displayed continuously without blinking. In this state, pressing the up/down keys 153, 154 will not change the tag. Then, the processor 140 initiates storage of the associated, confirmed tag with regard to the recent measurement value in the data storage 130 via receiving unit 120.

If in step 380 the processor 140 cannot find any range for tagging pre-selection or the fasting window which refers to the time information of the time stamp of the present measurement value, the no-tag is automatically selected.

After pressing the confirmation key 152, if the user presses the confirmation key again, the tag will start flashing again and pressing the up/down key will again allow the user to change the tag as explained above.

Further, in the "Logbook" mode the user is allowed to change the tag in the above explained manner but only within a predefined time range from the associated time stamp of the blood glucose measurement value, for example within 10 days. In case of the fasting tag, the user is allowed to change the tag into the fasting tag only within the predefined fasting window around the predefined usual fasting time at the same day.

If the time stamp of the recent measurement value falls within the fasting window around the usual fasting time and there is already a measurement value of that day marked as fasting the user is asked which measurement value shall be associated to the fasting tag. After selection of one of the measurement values as the fasting value the selection is confirmed by the user.

Further, if, for example the fasting window around the usual fasting time overlaps with, for example the time range for (pre-meal) breakfast, the fasting tag has priority over the (pre-meal) breakfast tag. Hence, in this case, if no fasting value is recorded for that day, the fasting tag is automatically selected if the time stamp of the present measurement value lies within the fasting window around the usual fasting time and the time range for pre-meal breakfast.

In another embodiment a flashing tag may not only be confirmed by the user by pressing the confirmation key 152 but also by removal of the strip from the port 112 after a blood glucose test, or when the medical device goes into sleep mode.

In the next optional step 390 a comment to the present measurement value may be selected by the user using the up and down keys 153, 154. The comment may then be confirmed with the confirmation key 152, wherein the chosen comment is then stored in the data storage 130 associated to the present measurement value as well.

Alternatively or additionally, the user may be asked in step 390 whether there are hypoglycemic events (hypos) are occurred and, if yes, which number, and/or whether there are hyperglycemic events (hypers) are occurred and, if yes, which number, since last measurement or last use of the medical device 100. Alternatively or additionally the user has to provide the information about the size of the injected medicament dose after a predetermined point in time, e.g. last use of the medical device or the time stamp of the last (previous) measurement value, wherein preferably the injected medicament dose is automatically selected as the dose of the last (previous) suggested dose by a titration method.

When the medical device 100 is in the "Measure BG" mode, the device may then turn into the sleep state (step 400) automatically after for example 120 seconds without any new action. Once the device has returned a new measurement value, the device turns to the sleep state automatically after for example 60 seconds without any user interaction.

As explained above the medical device 100 provides at least one memory review mode which is called "Logbook" mode. The respective display and calculations are explained in the following. The "Logbook" mode is entered when the user activates the medical device 100 by pressing e.g. the confirmation button 152. Then a display as depicted in FIG. 3 is shown.

In the "Logbook" the measurement values are preferably displayed in the order in which the entries are entered into the device, or alternatively according to the time and date assigned to the measurement values. In particular the most recent blood glucose measurement value is shown upon entry into the "Logbook" mode. Pressing the up and down keys 153, 154 the user may scroll through the records, for example by pressing the down key 153 the user may scroll backwards in time and by pressing the up key 154 the user scrolls forward in time.

Figure 3:
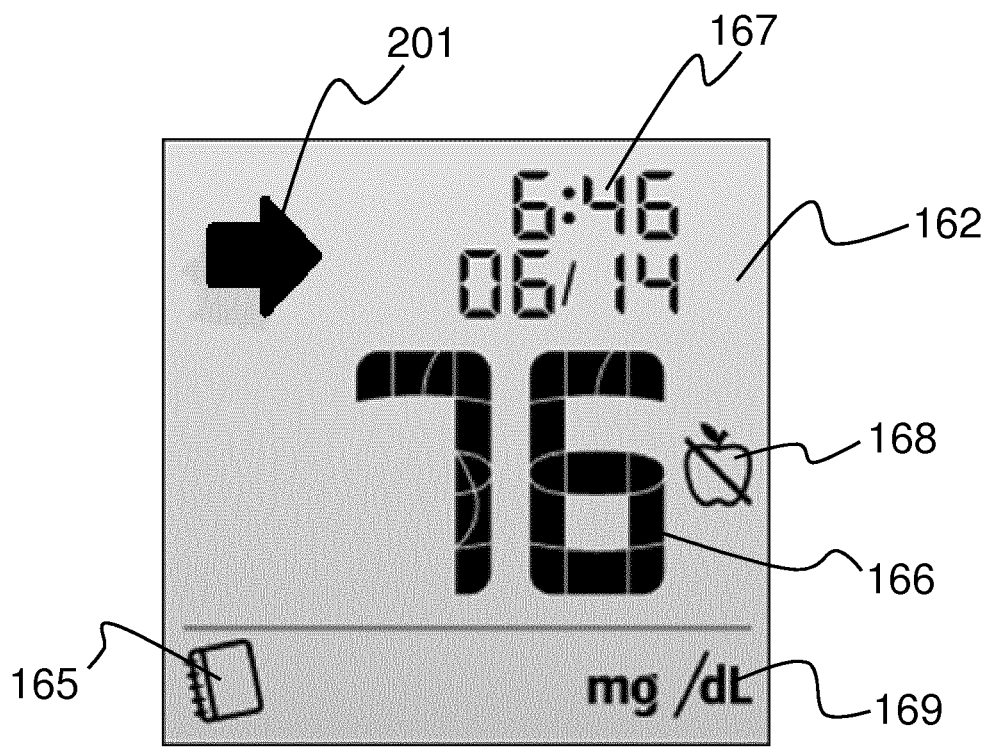
FIG. 3 depicts an example of the display of the medical device as shown in FIG. 1 in a "Logbook" mode.

One Example of a display 162 showing a measurement value is depicted in FIG. 3. The user knows from the "Book" sign 165 in the lower left corner of the display that he/she has entered the "Logbook" mode.

The display 162 in the "Logbook" mode further shows the blood glucose measurement value 166 as biggest number in the center of the screen. Above the measurement value 166 the associated time stamp 167 including date and time is displayed. On the right side the associated tag as a sign 168 is provided, wherein the sign may show for example an empty, struck out apple as shown at reference number 168 in FIG. 3 in case of an associated fasting tag, a full apple as shown in FIG. 4*b*) in case of an associated pre-meal tag, a bitten apple as shown in FIG. 4*c*) in case of an associated post-meal tag or a struck out circle as shown in FIG. 4*a*) in case of an associated no-tag. Additionally, in the lower right corner of the display 162 the measurement unit 169 for the blood glucose value is provided. A trend information may be provided by an arrow as shown at reference number 201 at the upper left corner of the display 162 in FIG. 3.

In the "Titration" or "Dose Helper" mode the user is provided with a dose suggestion preferably for basal insulin or analog if some of predefined conditions are fulfilled. The method used in this mode is based on at least the most recent fasting glucose value and other information like number of hypers and hypos and/or previous doses. Hence, in this mode the user is asked, in case there are two fasting measurement values within one single day tagged with the fasting tag, which fasting blood glucose measurement value has to be used for the titration algorithm. Further, additional data are requested from the user like

- occurrence or number of hypoglycemic events after a predetermined point in time, e.g. a last use of the medical device or the time stamp of the last (previous) measurement value,
- occurrence or number of hyperglycemic events after a predetermined point in time, e.g. the last use of the medical device or the time stamp of the last (previous) measurement value,
- size of the injected medicament dose after a predetermined point in time, e.g. the last use of the medical device or the time stamp of the last (previous) measurement value, wherein preferably the injected medicament dose is automatically selected as the dose of the last (previous) suggested dose.

From these data the "Dose Helper" determines whether the actual dose must be changed and provides the user with a proposal of a dose change or of a new dose, if applicable.

Figure 6:
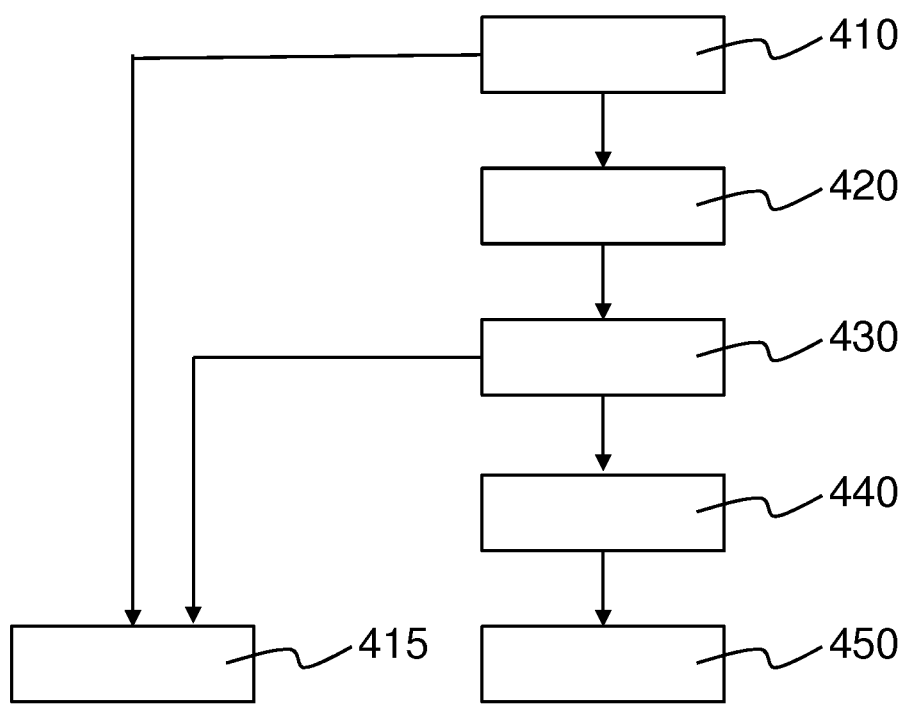
FIG. 6 shows a flow diagram of a method realized by the inventive medical device in the "Titration" mode.

The dose helper functionality may be started by choosing the mode "Titration" by means of the confirmation key 152. This functionality is described by means of the diagram as depicted in FIG. 6. After starting the functionality displays an initial screen in step 410 using display unit 160. After that in the next step 420 the user is asked at least one question regarding for example hypoglycemia symptoms, low blood sugar measurements (e.g. lower than 70 mg/dl) and/or taken insulin doses. Therein, the total number of questions depends on the answer to certain questions. After finishing questioning, in step 430 the device determines an insulin dose, preferably a dose of long-acting insulin, wherein the dose is determined by the processor 140, and displays the determined dose suggestion in the display of the display unit 160. Alternatively, in step 430 a message is displayed that no dose suggestion can be given to the user at this time.

The dose suggestion is determined by the processor 140 preferably based on previous fasting FBG values and/or other measured blood glucose values, previous administered insulin doses and/or other lifestyle information like hypoglycemia symptoms or low blood sugar values. Additionally, exercise information, nutrition facts and additional fast-acting insulin doses as well as stress information may be considered. In particular, it is determined whether a single value of FBG or a mean value FBG is within a target blood glucose range which was previously defined for the certain user. If the single or mean FBG value is above the target range, usually a dose increase is suggested, if the single or mean FBG value is below the target range, a dose decrease may be suggested.

The display 162 of display unit 160 in step 430 may provide the possibility that the proposed insulin dose is confirmed and saved in case the user immediately administers the suggested dose. In this case the suggested and administered dose is saved in data storage 130. Alternatively, the user may change the suggested dose and save it after administration.

Additionally, in step 410 it may be checked whether the current time is within a predefined time interval from the last known dose or the last dose is entered with a time less than the predefined time interval, preferably 18 hours, from the current time. In this case, the step 420 may be skipped and the display of display unit 160 may show the message that dose helper is unavailable because it is too close to the last insulin dose, or the dose helper may ask another question regarding the time of the last dose. In this embodiment it is assumed that the dose helper functionality is only used in close temporal proximity of dose administration.

Additionally or alternatively, for dose administration/using the dose helper a certain time or time range of day may be predefined. For example, the usual dose time may be predefined at 7 p.m. and the dose time window at +/−3 hours (i.e. between 4 p.m. and 10 p.m). In this case, another check whether the current time is between 4 p.m. and 10 p.m. may be performed using clock unit 180 during step 410. If the current time is outside this range, again, step 420 may be skipped and the display of display unit 160 may show the message that dose helper is unavailable because it can only be run at the usual dose time. Additionally, a warning message is sent to the user that the dose helper is run outside the dose time window around the usual dose time. In a preferred embodiment the time and date at which the user requested the dose helper outside the dose time window or for all requests, are stored in the data storage 130.

In the settings mode the usual dose time and the dose time window may be changed by the user at any time.

In another embodiment the processor 140 may check, how many dose helper requests (requests to run the dose helper in the titration mode) were executed during a predefined time period (stored in data storage 130, e.g. 1 month) outside the dose time window around the usual dose time. If the number of such dose helper requests exceeds a predefined maximum number (e.g. 7), the processor 140 initiates that the display 162 shows a message to the user suggesting a shift of the usual dose time. That means, if the user consistently runs the dose helper outside the dose time window a change of the usual dose time is proposed. Therein, the processor may calculate a new usual dose time value based on the previous data regarding the time of dose helper requests, preferable within the predefined time period, for example as a mean (Arithmetic mean value) value of the times of all dose helper requests within the predefined time period and shows this new usual dose time at the display 162 for user confirmation. If the user confirms this new usual dose time value he/she thereby automatically changes this value. Thereby, the usual dose time is adjusted based on the use pattern of the dose helper.

In a further preferred embodiment, the processor initiates the display 162 to show a dose reminder which reminds the user to run the dose helper and to take the daily (long-acting) insulin dose. The reminder is triggered after a predefined part, for example half, of the dose time window around the usual dose time has passed if the dose helper has not been used within the preset dose time window on the current day.

The displayed message may be accompanied by a sound or tactile information (like vibration). In case the dose helper was run at the same day, the reminder will appear only if the dose helper was not finished at the same day. The reminder only appears within the predefined dose window around the usual dose time.

In order to run the dose helper functionality correctly and successfully it is preferred that the blood glucose measurement values which are FBG values are identified. Therefore these blood glucose measurement values may be tagged by the user. In order to make the tagging easier for the patient the tagging may be realized by defining a usual fasting time (e.g. 7:00 a.m.) and a certain fasting window (e.g. +/−3 hours around the usual fasting time, e.g. 4:00 a.m. to 9:59 a.m.) which are stored in the data storage 130 and may be changed by the user in the settings mode at any time. If the usual fasting time is changed in the settings mode, the predefined usual meal times stored in the data storage 130 may be changed as well. Therefore, the usual meal times are shown to the user at the display 162 for confirmation or adaption by the user.

A blood glucose measurement value detected within this time interval receives the pre-tagging "FBG value". The user now only needs to confirm this tag, for example by using the soft key 152. Now, the measured blood glucose measurement value is stored in the data storage 130 as a FBG value along with the date and time of the measurement. If the user does not confirm this pre-tagging, no tag is stored along with this value. Preferably, the user may choose other tags such as "pre meal" or "after meal", for example by using the keys 153, 154.

In a preferred embodiment at the display 162 a predefined fasting definition screen is shown at first time the user confirms a fasting tag with regard to a measurement value. The fasting definition screen provides information to the user that the user understands what to tag a reading as "fasting". This avoids incorrectly tagged fasting readings and more reliable dose suggestion. The data for the fasting definition screen may be stored in the data storage 130. Additionally, the fasting definition screen may be shown if a reading is tagged at a minimum of a predefined outside fasting time interval (e.g. two hours outside the predefined fasting window around the usual fasting time) or from the usual fasting time (e.g. 6 hours from the usual fasting time). The user has to confirm that he/she has read and understood the fasting definition screen. This may be also a necessary condition for receiving a dose suggestion in the "Titration" mode.

For further explanation and possibilities with regard to the dose helper functionality and the blood glucose measurement the disclosure of WO 2010/89304 A1 is incorporated herein by reference.

In cases where the data set is not sufficient or inadequate to calculate an insulin dose because, for instance, the patient does not take measurements regularly or does not store the administered insulin doses, the dose helper functionality of the device may display the message that no recommendation can be provided until an adequate data set is established. Further, a dose recommendation cannot be given if the patient is in a situation where a preemptive dose change is required based on other factors (e.g. illness, change of other diabetes medication, change in lifestyle, exercise, vacation) and time changes due to travelling of more than a predefined time range, for example more than three hours.

It shall be emphasized that in a preferred embodiment the patient makes the final decision on a dosing. The result of the processor 140 may only be a suggestion in this case. The patient may confirm this dose or change it. The inventive device is seen as a support similar to the on-paper treatment algorithms for self-titration that may provide a direction. Still, the patient is taught to observe other rules for taking into account other factors like health, activity etc. in order to safely manage the insulin dosing, which may lead to the patient overruling the dose suggestion or calling their HCP if they are unsure.

Figure 7:
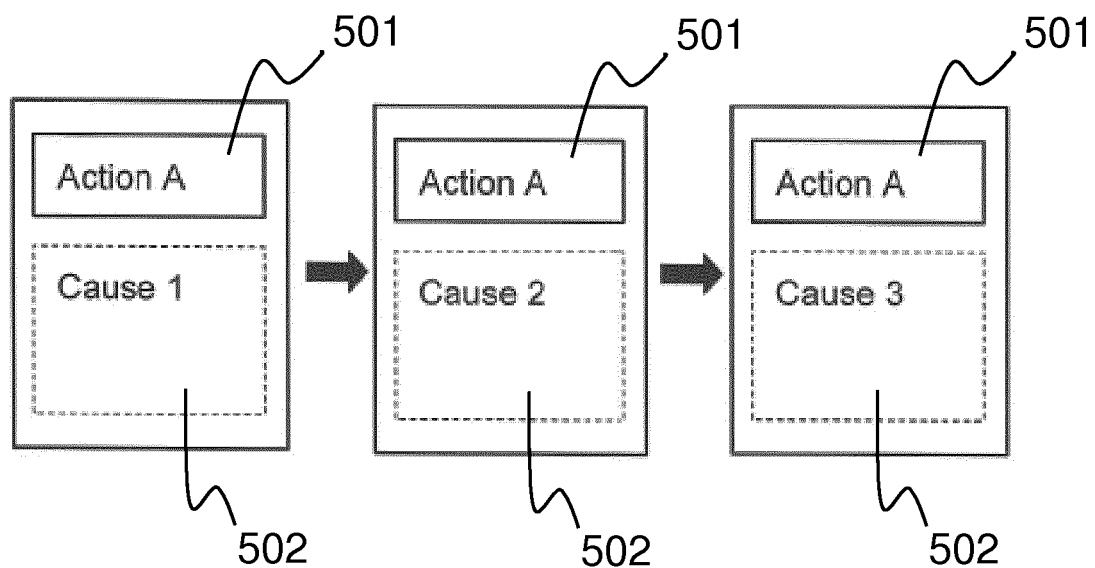
FIG. 7 depicts three different screens at the display of a conventional medical device.
Figure 8:
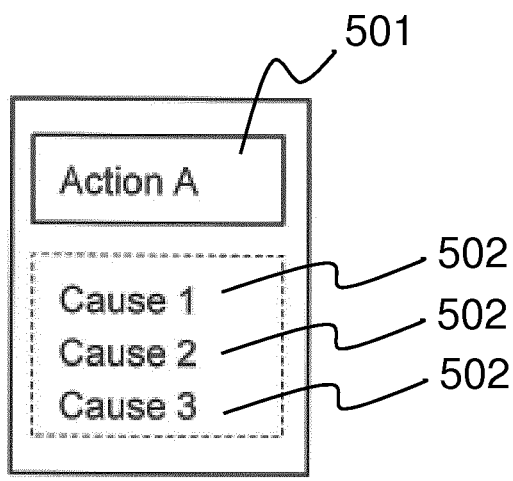
FIG. 8 depicts one screen at the display of the inventive medical device.

Regarding the information displayed to the user by the display 162 initiated by the processor 140 within all above modi of the device or processor 140 there are certain cases when specific conditions apply two or more secondary information 502 is displayed to the user together with the same primary information (e.g. "Call your HCP for assistance", 501, see FIG. 7) describing several reasons for that or circumstances. This is cumbersome for the patient causing that the user does not read all messages well enough since the instruction in the primary information is the same for all these messages. Therefore, if there is one primary information 501 and at least one secondary information 502 assigned thereto to be displayed, the processor 140 sends this information to the display 162 such that the primary information 501 and the secondary information 502 is displayed on the same screen. If there is two or more (different) secondary information 502 assigned with the primary information 501 to be displayed, the different secondary information 502 is collected and assembled and the primary information 501 is displayed only once with the at least two secondary information 502 at one screen (see FIG. 8).

In case more than two secondary information 502 are assigned to one primary information 501 and to be displayed the secondary information 502 may be displayed according to its priority with regard to importance for the user or user type. As user type for example the patient and the HCP may be distinguished. Therefore to each secondary information an importance level (1, 2, 3, etc.) may be assigned in the data storage 130, and in a preferred embodiment, an importance level for each user type may be assigned in form of a respective importance level matrix. For example the following may be assigned in the data storage:

| Secondary information | Importance level for patient | Importance level for HCP |
|---|---|---|
| CAUSE 1 | 2 | 1 |
| CAUSE 2 | 3 | 2 |
| CAUSE 3 | 1 | 3 |

In the display the secondary information is displayed according to its assigned importance level for the respective user type. If a patient uses the inventive device CAUSE 2 is displayed in the list on one display at first, then CAUSE 1 and after that CAUSE 3. In case an HCP uses the device, CAUSE 3 is displayed first (after the primary information), then CAUSE 2 and at least CAUSE 3. In case a secondary information 502 has the same importance level as another secondary information the information is displayed in alphabetical order.

As explained above in an example embodiment, device 100 may be realized as a two-part device, wherein the data storage 130, the receiving unit 120, the processor 140, the user input unit 150, the display unit 160 with the display 162, the interface unit 170, and the clock unit 180 form the data management unit and are realized in first part of the device like a smartphone or another computer separate from the measurement unit 110 forming the second part of the device. The inventive method runs as a software program (application or "app") on the hardware of the device. The keys 151, 152, 153 and 154 are realized in this case as button fields on the display of a touchscreen.

The invention claimed is:

1. A data management unit for supporting health control, the data management unit comprising:
a processor;
a data input unit adapted to input data and/or requests and connected to the processor;
a data storage connected to the processor, the data storage configured to store a group of tags comprising a fasting tag and at least one other event tag;
wherein the processor is adapted to receive new data from the data input unit or a measurement unit, wherein the new data comprises a recent measurement value of a body parameter,
wherein the data management unit further comprises a clock unit connected to the processor, wherein the clock unit assigns a time stamp to the new data,
wherein the processor is further adapted to select a tag from the group of tags and assign the tag to the new data, the tag referring to an event, wherein the processor is further adapted to assign the tag automatically or to automatically select the tag from the group of tags for assignment, wherein the processor is further adapted to assign the fasting tag to the new data only when the time stamp of the new data received is between a first time and a second time of a predefined fasting window, wherein the predefined fasting window is stored in the data storage,
wherein the data management unit is adapted to:
determine that the time stamp of the new data falls between the first time and the second time of the predefined fasting window;
determine that another measurement value is stored in the data storage along with a tag and a time stamp assigned to the other measurement value, wherein the time stamp assigned to the other measurement value and the time stamp assigned to the new data indicate the same day, wherein the tag assigned to the other measurement value stored in the data storage is the fasting tag;
in response to determining that the time stamp of the new data falls between the first time and the second time of the predefined fasting window and determining that the other measurement value is stored in the data storage, provide a request for a user to select which of the new data and the other measurement value shall be associated with the fasting tag; and
in response to receiving, from the user, a selection between the new data and the other measurement value, cause only one of the new data or the other measurement value corresponding to the selection to be assigned to the fasting tag.

2. The data management unit according to claim 1, further comprising a display connected to the processor and adapted to display received messages or information, wherein the display additionally displays, at least for the first time when the fasting tag is to be assigned to the new data via the data input unit, a predefined definition screen to provide information to the user indicating a condition for assigning the fasting tag to the new data, wherein the fasting tag assignment is completed in response to receiving a confirmation of the predefined definition screen from the user.

3. The data management unit according to claim 1, further comprising:
a display, the display and the clock unit being connected to the processor,
wherein the processor is adapted to provide a dose helper functionality comprising a titration method with regard to a predefined medicament, the titration method determining and/or recommending a medicament dose value or a corrective amount of the medicament dose value;
wherein the data storage is adapted to store a usual dose time and/or a dose time window, a predefined recommendation message, a time of a dose helper request, and a predefined criterion,
wherein the clock unit is adapted to determine a time of receiving a dose helper request received through the data input unit,
wherein the processor is further adapted to initiate storing the time of the dose helper request when the time is outside the usual dose time or outside the dose time window around the usual dose time,
wherein the processor is further adapted to execute the dose helper functionality only when a time of a most recent dose helper request is within the dose time window around the usual dose time, and
wherein the processor is further adapted to initiate sending the predefined recommendation message for change of at least one of the usual dose time and the dose time window to the display when a time distribution of a plurality of most recent dose helper requests within a predefined time period corresponds to the predefined criterion.

4. The data management unit according to claim 3, wherein the processor is further adapted to check whether a number of the plurality of most recent dose helper requests outside the dose time window is higher than a predefined maximum number during the predefined time period, wherein the predefined maximum number and the predefined time period are stored in the data storage.

5. The data management unit according to claim 3, wherein the processor is further adapted to generate and send a predefined warning message to the display when the processor receives, from the data input unit, a dose helper request that is outside the dose time window, wherein at least part of the predefined warning message is stored in the data storage.

6. The data management unit according to claim 3, wherein the processor is further adapted to calculate a modified value of at least one of the usual dose time and the dose time window based on one or more respective times associated with one or more of the most recent dose helper requests, wherein the predefined recommendation message recommends to change the at least one of the usual dose time and the dose time window according to a respective calculated modified value.

7. The data management unit according to claim 3, wherein the processor is further adapted to send a predefined reminder message to the display when a predefined part of the dose time window is passed at a current day without receiving the dose helper request or without finishing a requested dose helper functionality, wherein the reminder message is displayed at the display.

8. The data management unit according to claim 1, wherein the data storage stores predefined primary information and at least one predefined secondary information assigned to the predefined primary information, wherein the processor is further adapted to send the predefined primary information and the at least one predefined secondary information to a display, wherein the predefined primary information and the at least one predefined secondary information are displayed on one screen of the display.

9. The data management unit according to claim 8, wherein two or more secondary information are displayed on the one screen of the display, each of the two or more secondary information being displayed according to a respective priority with regard to importance of the secondary information for a respective user or a user type of the user to whom the two or more secondary information is being displayed.

10. A method for operating a data management unit for supporting health control, the method comprising:
receiving, by a data input unit adapted to input data and/or requests, new data, the data input unit being connected to a processor wherein the new data comprises a recent measurement value of a body parameter;
assigning, by a clock unit connected to the processor, a time stamp to the new data;
assigning a tag to the new data, the tag referring to an event and chosen from a group of tags stored on the data management unit, the group of tags comprising a fasting tag and at least one other tag, wherein the tag is assigned automatically or automatically selected from the group of tags for assignment by the processor, wherein the fasting tag can only be assigned to the new data when the time stamp of the new data is between a first time and a second time of a predefined fasting window, wherein the predefined fasting window is stored in a data storage connected to the processor;
determining that the time stamp of the new data falls between the first time and the second time of the predefined fasting window;
determining that another measurement value is stored in the data storage along with a tag and a time stamp assigned to the other measurement value, wherein the time stamp assigned to the other measurement value and the time stamp assigned to the new data indicate the same day, wherein the tag assigned to the other measurement value stored in the data storage is the fasting tag;
in response to determining that the time stamp of the new data falls between the first time and the second time of the predefined fasting window and determining that the other measurement value is stored in the data storage, providing a request for a user to select which of the new data and the other measurement value shall be associated with the fasting tag; and
in response to receiving, from the user, a selection between the new data and the other measurement value, causing only one of the new data or the other measurement value corresponding to the selection to be assigned to the fasting tag.

11. The method according to claim 10, further comprising additionally displaying, at least for the first time when the fasting tag is to be assigned to the new data via the data input unit, by a display connected to the processor, a predefined definition screen to provide information to the user indicating a condition for assigning the fasting tag to the new data, wherein the fasting tag assignment is completed in response to receiving a confirmation of the predefined definition screen from the user.

12. The method according to claim 10, wherein a usual dose time and a dose time window, a predefined recommendation message, a time of a dose helper request, and a predefined criterion are stored in the data storage, and the method further comprises:

providing, by the processor, a dose helper functionality comprising a titration method with regard to a predefined medicament, the titration method determining and/or recommending a medicament dose value or a corrective amount of the medicament dose value;
determining, by the clock unit, a time of receiving a dose helper request received through the data input unit;
initiate, by the processor, storing the time of the dose helper request when the time is outside the usual dose time or outside the dose time window around the usual dose time,
wherein the processor is adapted to execute the dose helper functionality only when a time of a most recent dose helper request is within the dose time window around the usual dose time; and
initiating, by the processor, sending a recommendation message for change of at least one of the usual dose time and the dose time window to a display when a time distribution of a plurality of most recent dose helper requests within a predefined time period corresponds to the predefined criterion.

13. The method of claim 12, wherein the processor is further adapted to check whether a number of the plurality of most recent dose helper requests outside the dose time window is higher than a predefined maximum number during the predefined time period, wherein the predefined maximum number and the predefined time period are stored in the data storage.

14. The method of claim 12, further comprising sending, by the processor, a predefined warning message to the display when the processor receives, from the data input unit, a dose helper request that is outside the dose time window, wherein at least part of the predefined warning message is stored in the data storage.

15. The method of claim 12, further comprising calculating, by the processor, a modified value of at least one of the usual dose time and the dose time window based on one or more respective times associated with one or more of the most recent dose helper requests, wherein the recommendation message recommends to change the at least one of the usual dose time and the dose time window according to a respective calculated modified value.

16. The method of claim 12, further comprising:
sending, by the processor, a predefined reminder message to the display when a predefined part of the dose time window is passed at a current day without receiving the dose helper request or without finishing a requested dose helper functionality; and
displaying the reminder message.

17. The method of claim 10, wherein the data storage stores predefined primary information and at least one predefined secondary information assigned to the predefined primary information, and the method further comprises:
send, by the processor, the predefined primary information and the at least one predefined secondary information to a display; and
displaying the predefined primary information and the at least one predefined secondary information on one screen of the display.

18. A non-transitory, computer-readable medium storing one or more instructions executable by a computer system to perform operations for supporting health control, the operations comprising:
receiving, by a data input unit adapted to input data or requests, new data, the data input unit being connected to a processor, wherein the new data comprises a recent measurement value of a body parameter;

assigning, by a clock unit connected to the processor, a time stamp to the new data;

assigning a tag to a new data received from the data input unit, the tag referring to an event and chosen from a group of tags comprising a fasting tag and at least one other tag, wherein the tag is assigned automatically or automatically selected from the group of tags for assignment by the processor, wherein the fasting tag can only be assigned to the new data when the time stamp of the new data is between a first time and a second time of a predefined fasting window around a predefined usual fasting time, wherein the predefined fasting window, the predefined usual fasting time, and the group of tags are stored in a data storage connected to the processor; and determining that the time stamp of the new data falls between the first time and the second time of the predefined fasting window;

determining that another measurement value is stored in the data storage along with a tag and a time stamp assigned to the other measurement value, wherein the time stamp assigned to the other measurement value and the time stamp assigned to the new data indicate the same day, wherein the tag assigned to the other measurement value stored in the data storage is the fasting tag;

in response to the determining that the time stamp of the new data falls between the first time and the second time of the predefined fasting window and determining that the other measurement value is stored in the data storage, providing a request for a user to select which of the new data and the other measurement value shall be associated with the fasting tag; and in response to receiving, from the user, a selection between the new data and the other measurement value, causing only one of the new data or the other measurement value corresponding to the selection to be assigned to the fasting tag.

\* \* \* \* \*